United States Patent [19]

Eberle et al.

[11] 4,033,176

[45] July 5, 1977

[54] POCKET-SIZED, DIRECT-READING ULTRASONIC THICKNESS GAUGE

[75] Inventors: Frederick L. Eberle, Hammond, Ind.; Bernard Ostrofsky, Naperville, Ill.

[73] Assignee: Standard Oil Company (Indiana), Chicago, Ill.

[22] Filed: July 11, 1975

[21] Appl. No.: 595,060

[52] U.S. Cl. ............................................. 73/67.9
[51] Int. Cl.² .................................... G01N 29/00
[58] Field of Search .............. 73/67.9, 67.8 R, 67.7

[56] References Cited

UNITED STATES PATENTS

| | | | |
|---|---|---|---|
| 2,562,450 | 7/1951 | DeLano, Jr. ................... | 73/67.9 X |
| 3,238,767 | 3/1966 | Clynes ............................ | 73/67.9 |
| 3,256,733 | 6/1966 | Carlin ............................. | 73/67.8 |
| 3,262,306 | 7/1966 | Henry ............................. | 73/67.9 |
| 3,427,866 | 2/1969 | Weighart ........................ | 73/67.9 X |
| 3,690,154 | 9/1972 | Wells et al. .................... | 73/67.9 |
| 3,748,895 | 7/1973 | Kummer et al. ................ | 73/67.9 |

*Primary Examiner*—Jerry W. Myracle
*Attorney, Agent, or Firm*—Frank J. Sroka; Arthur G. Gilkes; William T. McClain

[57] ABSTRACT

This invention relates to a method and apparatus for measuring the time interval between two or more sequential signals. One particular application is measuring the time interval between pulses in non-destructive ultrasonic testing. A time-variable gate is used to effectually span the time interval between signals, the interval of the gate corresponding to the time interval between signals.

19 Claims, 2 Drawing Figures

POCKET-SIZED, DIRECT-READING ULTRASONIC THICKNESS GAUGE

BACKGROUND

This invention relates to an electronic time base measurement circuit and in one of its aspects to an electrical circuit for performing such measurements in an ultrasonic inspection system.

Application of a voltage pulse to a piezoelectric crystal will cause it to mechanically oscillate at its resonant frequency. Sound, at the resonant frequency of the crystal will, when it strikes the crystal, also cause oscillation. When the crystal oscillates, it generates a sinusoidal voltage and a high frequency sound wave, both of which occur at the crystal's resonant frequency.

In ultrasonic flaw-detector and thickness measuring instruments, a piezoelectric crystal (transducer) is placed on or near the surface of the material whose integrity or thickness is to be measured. In order to insure effective coupling between the transducer and the surface, the space between may be filled with an acoustically transparent material, i.e., a material having a small amount of accoustical attenuation such as water or oil. The output of a pulse generator, consisting of short duration voltage pulses, is applied to the crystal. In thickness measuring instruments, high frequency sound generated by the crystal when it is pulsed passes through the material, is reflected from the opposite surface, and returns to the crystal where the back-reflected sound causes the crystal to again oscillate. The same sequence of events may happen repeatedly and there may be a second, third or even greater number of back-reflections due to the same voltage pulse. The voltage pulse initiating this sequence is called the initial pulse. By measuring the elasped time between the initial pulse and a back-reflection or between two back-reflections, and knowing the velocity of sound through the material being tested, the thickness can be determined.

In ultrasonic pulse-echo applications it is often desirable to accurately measure the time required for the transmitted pulse to traverse the material under test, be reflected by the back surface or a defect within the material, and return to the receiving transducer. This time measurement may be used to calculate the thickness of the material or the location of a defect. Due to the high velocity of sound in most materials, this time measurement must be made very precisely if thickness measurements are to be performed with acceptable accuracy. For example, a timing error of one millionth of a second can result in a calculated thickness in error of about one-sixteenth inch in steel.

Ultrasonic pulse-echo thickness measurement apparatus generally consists of a highly damped piezoelectric transducer excited by an ultrasonic pulse generator connected thereto, injects ultrasonic pulses of short duration into a specimen such as a plate metal, to determine the thickness D thereof. After entering the specimen, the ultrasonic pulse is repeatedly reflected back and fourth between the parallel surfaces of the specimen separated by the dimension D until its energy is dissipated. During this reverberation process, piezoelectric transducer which also acts as an ultrasonic receiver, generates a short voltage pulse each time the ultrasonic pulse strikes upon the specimen surface to which the piezoelectric transducer is coupled. Thus, following the emission of the initial excitation pulse, a sequence of electrical pulses is produced by the piezoelectric transducer. The time interval T between two consecutive pulses of this sequence is equivalent to the specimen thickness according to $$T = 2D/V_L$$

where $V_L$ represents the longitudinal ultrasonic wave velocity in the material of the specimen. For a specific material, the longitudinal ultrasonic wave velocity is usually constant within a wide range of ultrasonic frequencies and the specimen thickness D can be determined by measuring the pulse period T or its reciprocal.

The time interval between the initial pulse and a back-reflection or between various reflection pulses can be determined by displaying on an oscilloscope the sinusoidal voltage across the crystal corresponding to the initial pulse and back-reflections. Thickness of the material being tested was then read on the horizontal or time axis of the oscilloscope. A more recent development is the direct-reading instrument which displays thickness measurements directly on a meter or on a digital read-out display. In the direct-reading instrument, a constant current source is used to charge a capacitor at a linear rate with respect to time. The constant current source is gated-on by the initial pulse and gated-off by the first back-reflection. The charge on the capacitor is, therefore, dependent on the elapsed time between the initial pulse and the first back-reflection which, in turn, depends on the thickness of the material. The charge on the capacitor at any time is indicated on a meter or a digital-type display. The readout, whether meter or digital-type, is calibrated directly in inches. Both the oscilloscope and direct-reading type instruments require considerable electronic circuitry and, as a consequence, have a large physical size. Both of these instruments are also relatively expensive.

This invention provides a simple and novel method and apparatus for measuring the elapsed time between two consecutive signals and is not limited to ultrasonic testing. In one specific embodiment, it provides a method and apparatus for measuring the elapsed time between an initial pulse and the first back-reflection or between various reflection pulses in ultrasonic testing. The apparatus is less expensive and much smaller than the instruments currently in use. This invention provides an accurate ultrasonic thickness measuring device which is made from simple, inexpensive electronic components and which can be easily hand held.

SUMMARY OF THE INVENTION

This invention provides a method and apparatus for measuring the time interval between two or more sequential signals. One particular application is measuring the time interval between pulses in non-destructive ultrasonic testing. A time-variable gate is used to effectually span the time interval between signals, the interval of the gate corresponding to the time interval between signals.

The method and apparatus of this invention is based upon the use of a time-variable gate which can be implemented a number of ways. In one such implementation, two or more sequential signals are received and a response signal is sent in response to the received signals. A time-variable gate controls the sending of the response signal so that the response signal will be sent corresponding to a discrete number of received signals. For example, two or more sequential signals are received and then amplified by an amplification means. The ON/OFF condition of the amplification means is controlled by a time-variable gate so that the amplification means is switched ON for a time just sufficient to amplify the received signals. The time during which the gate switches the amplification means ON corresponds to the elapsed time between the signals.

This method and apparatus provides a simple and novel method of measuring the elapsed time between the initial pulse and the first back-reflection in an ultrasonic thickness measuring instrument: A piezoelectric crystal is pulsed in the usual way. The resulting initial pulse and associated back-reflections are amplified and fed to a pulse counter. The output of the counter is a current, which is displayed on a meter. The amount of current corresponds to the number of input pulses to the counter. A variable-width square wave generator supplies a square wave, which gates the amplifier ON from a normally OFF condition. The duration of the square wave can be varied by means of a potentiometer so that the amplifier is gated-on for only the time necessary to amplify the initial pulse and first back-reflection. This is indicated on the meter as a current corresponding to two pulses. The duration of the square wave then corresponds to the elapsed time between the initial pulse and the first back-reflection. Since the potentiometer controls the duration of the square wave, it can be calibrated directly in units of time or material thickness.

The most common means of generating square wave is through use of a multivibrator which can develop a wave, thereby switching a piece of equipmebt ON or OFF in less than a few milliseconds, preferably less than 1/10 of a microsecond.

A multivibrator is essentially two stages of resistance-capacitance-coupled amplification with output connected to input. Usually the coupling is between the plates and the grids, but cathode coupling may also be used. Any casual disturbance in the potential of the first grid is amplified and reversed in polarity by the two stages. The two reversals of polarity produce, at the first grid, a signal of large magnitude and the same polarity so that initially assumed. Consequently the potential of the first grid is rapidly shifted, by cumulative action, in the direction of the first disturbance. If the disturbance was negative, the first stage becomes non-conducting or is "cut off", usually in a few millionths or thousandths of a second. In this case, the plate of the first stage is raised in potential, driving the grid of the second stage sharply positive and holding the second stage at full conduction. If the initial disturbance was positive, the first stage reaches full conduction at once, while the second stage is cut off.

During the ensuing period, charge trapped on the cutoff grid leaks off at a rate determined by the capacitance and resistance connected to it, usually in a time comparable with RC where R = grid resistance to ground in ohms and C = coupling capacitance in farads. When the cutoff grid is raised in potential to the conduction level, the continuing rise in the potential becomes a positive disturbance in the sense first assumed, and the first stage is thereby rapidly driven to full conduction, while the second stage, depressed by the fall in the first-stage plate potential, is cut off. In this manner the two stages exchange roles, one being cut off while the other is fully conducting, the exchanges being separated by a time approximately equal to the time constant of the coupling connection.

The waveform taken from either plate has a rectangular shape in the upper, positive portions and an exponential shape in the lower, negative portions. If both coupling circuits have the same time constant, the duration of positive and negative portions in the same (symmetrical multivibrator). By suitable choice of the time constants, it is possible to vary the relative duration of the two portions and, in effect, to produce short, sharp pulses separated by longer quiescent intervals.

DESCRIPTION OF THE DRAWINGS

As shown in the block diagram. FIG. 1, the output of a unijunction pulse generator 1 is used to trigger a SCR (silicon controlled rectifier) pulser 2. The output of the pulser 2 causes the piezoelectric crystal 3 to oscillate at its resonant frequency. Bursts of crystal oscillation, due to both the pulser and the back-reflections from the sample 4, are amplified and rectified in the amplifier 5 and detector 6 stages, respectively. The amplified and rectified signal is fed to the pulse counter 7 which converts the number of bursts of crystal oscillation per second to an equivalent current which is displayed on a meter 8.

At the same time the pulser pulses the piezoelectric crystal and causes it to oscillate, it also starts the variable-width square-wave generator. The output of the variable-width square-wave generator 9 is used to gate the amplifier 5 ON from its normally OFF condition. The width of the square-wave is adjusted by means of a potentiometer so that the amplifier 5 is gated ON for only the minimum time necessary to amplify the crystal oscillation burst due to the pulser (initial pulse) and the first back-reflection. This is indicated on the meter 8 as a current twice as large as is obtained from the initial pulse alone. Since the elapsed time between the initial pulse and the first back-reflection is directly proportional to the thickness of the sample, the potentiometer in the variable-width square-wave generator can be calibrated directly in inches.

Figure 1:
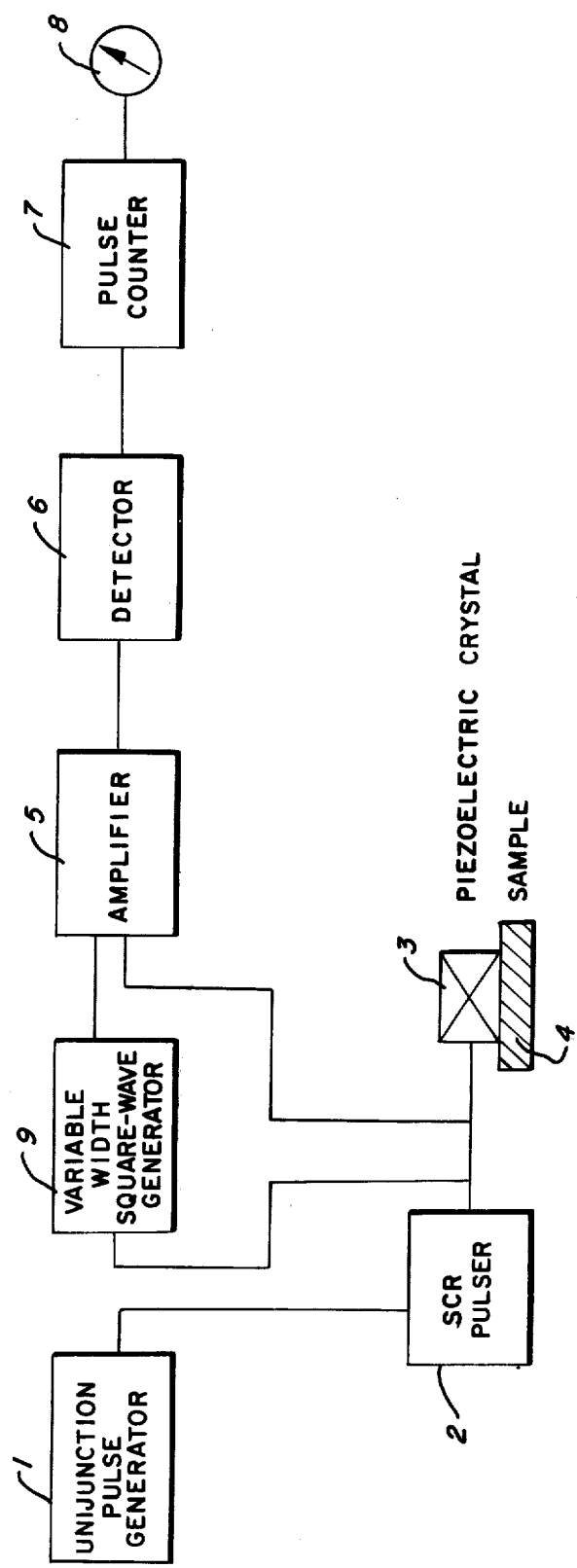
FIG. 1 is a block diagram of an ultrasonic thickness measuring device employing the disclosed apparatus for measuring time intervals between sequential signals.
Figure 2:
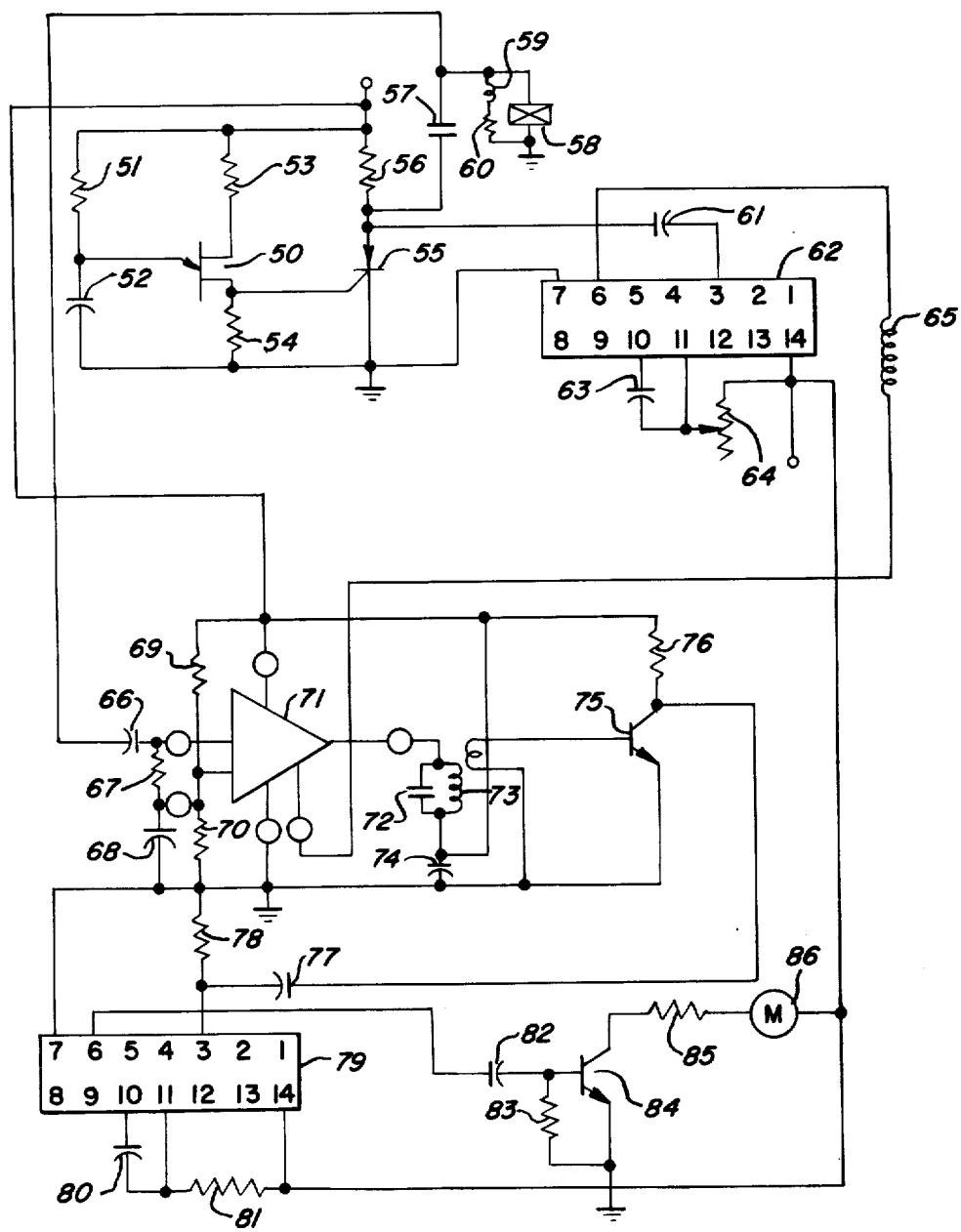
FIG. 2 is a schematic diagram of the same device.

In FIG. 2, the pulse generator uses a 2N2647 unijunction transistor 50 as a relaxation oscillator. A 10,000 ohm, ½ watt carbon resistor 51 and a 0.022 microfarad Mylar capacitor 52 establish a pulse repetition rate of 360 pulses per second. A 270 ohm, ½ watt carbon resistor 53 functions as a temperature compensating resistor. Through pulse generator output resistor 54, a 27 ohm, ½ watt carbon resistor, a positive pulse is provided for triggering the 2N4149 silicon controlled rectifier (SCR) 55. The variable-width, square-wave generator is triggered by the SCR pulser 55. Pulser load resistor 56 and pulser to transducer coupling capacitor 57 are provided by a 3300 ohm, ½ watt carbon resistor and by a 0.002 microfarad disc ceramic capacitor, respectively.

The above described pulse generator and SCR pulser provide a pulse for exitation of transducer 58 which is a 5 megahertz lead metaniobate crystal. Transducer tuning inductor 59 and transducer tuning resistor 60 are provided by a 0.7 microhenry inductor and a 2.2 ohm, 1 watt carbon resistor respectively.

The above described pulse generator and SCR pulser also provide a pulse for triggering the variable-width square-wave generator. The pulser is connected to the square-wave generator through coupling capacitor 61 which is a 500 picofarad disc ceramic capacitor. The variable-width square-wave generator is a monostable multivibrator consisting of an Motorola MC 74121F integrated circuit 62. Connected thereto, a 0.022 microfarad mylar capacitor 63 and a 2000 ohm, linear taper potentiometer 64 are used to determine the width of the square wave. Use of the potentiometer permits the width to be varied from 0 to approximately 20 microseconds. A 1.0 millihenry inductor 65 is provided for shaping the gate signal.

Signals received by the transducer 58 are sent to the amplifier 71 through a coupling capacitor 66 and a coupling resistor 67 which are a 0.001 microfarad, mylar capacitor and a 1000 ohm, ½ watt carbon resistor, respectively. A 0.01 microfarad mylar capacitor serves as R. F. bypass capacitor 68. Resistors 69 and 70 are voltage dividers consisting of 1000 ohm, ½ watt and 2200 ohm, ½ watt carbon resistors, respectively. The output of the variable-width square-wave generator 62 is applied to the amplifier 71 through gate signal shaping inductor 65 and controls the ON/OFF condition of the amplifier. R. F. amplifier 71 is an RCA CA 3028A differential amplifier integrated circuit. The amplifier circuit amplifies the oscillations from the piezoelectric crystal when in an ON condition and passes the output through an amplifier output capacitor-inductor circuit comprising a 120 picofarad silver mica capacitor 72 and a 8.5 microhenry inductor with coupling link 73. R. F. bypass capacitor 74 is provided by a 0.01 microfarad mylar capacitor ohm, a 2N1308 transistor. The amplifier output is link-coupled to the base of the detector transistor 75. The detector load resistor is a 1200 ohm, ½ watt carbon resistor 76.

The detector is coupled to a square wave generator 79 by a 500 picofarad silver mica capacitor 77 and 33,000 ohm, ½ watt carbon resistor 78. The pulse counter consists of an MC 74121F monostable multivibrator 79 and a 2N5172 counter transistor 84. Square-wave width capacitor 80 and resistor 81 are provided by a 0.001 microfarad mylar capacitor and a 1500 ohm, ½ watt carbon resistor, respectively. For each trigger pulse from the detector, the multivibrator 79 produces a single square-wave of constant amplitude and duration. The duration is approximately 1.0 microsecond and is determined by capacitor 80 and resistor 81.

The square-wave generator is coupled to the counter transistor 84 by coupling capacitor 82 and coupling resistor 83, which are a 10 microfarad tantalum capacitor and a 1 megohm, ½ watt carbon resistor, respectively. Output of the square-wave generator passes to counter transistor 84 and then through counter load resistor 85, a 1000 ohm, ½ watt carbon resistor. This signal is displayed on counter meter 86, a 20 microampere microammeter.

The output from the unijunction pulse generator 50 is a 3 volt positive pulse occurring at a rate of 360 pulses per second. This pulse triggers the SCR pulser 55 to produce a negative pulse 9 volts in amplitude. The pulser output causes the variable-width square-wave generator 62 to generate a 4 volt positive square-wave.

The voltage across the piezoelectric crystal 58 consists of a succession of damped 5 MHz oscillations due to the initial pulse from the pulser 55 and the multiple back-reflections from the sample. After amplification, only the initial pulse and first back-reflection are present. This is because the width of the square-wave gating signal applied to amplifier 71 was adjusted so that the amplifier was gated-on only long enough to amplify the initial pulse and first back-reflection.

From the amplifier 71, the signal passes through the detector stage where it is rectified and the RF removed. The signal at the output of detector 75 consists of negative pulses which, after shaping in an RC network, are used to trigger square-wave generator 79 in the pulse counter.

For each trigger pulse, the square-wave generator 79 produces a single square-wave having an amplitude of positive 4 volts and a duration of approximately 1 microsecond. The duration and amplitude of each square-wave is constant and is independent of the shape and amplitude of the trigger pulse. This ensures that, for all samples, the counter transistor 84, which is fed by the square-wave generator, registers the same current reading on the meter for the initial pulse and first back-reflection.

To make a thickness measurement, the transducer is placed against the sample with an oil couplant between sample and transducer. The time variable gate is slowly opened, that is lengthened in time, until the counter meter abruptly changes from 0 to 5 MA when the initial pulse is gated-in and from 5 to 10 MA with the first back-reflection. At this point, the time variable-gate is open to a width or rather time which corresponds to the time between the initial pulse and first back-reflection and the time can be determined by simple calibration of the potentiometer used to vary the time-variable gate.

We claim:

1. A method for measuring the time between two or more sequential signals which comprises:
receiving two or more sequential signals; sending a response signal in response to the received signals; controlling the sending of the response signal by a variable-width square wave gate; adjusting the width of the variable square wave gate so that the response signal will be sent corresponding to a discrete number of received signals; and measuring the duration of the gate.

2. A method for measuring the time between two or more sequential signals which comprises:
receiving two or more sequential signals;
amplifying the signals by an amplification means; controlling the ON/OFF condition of the amplification means by adjustment of a time-variable gate so that the time-variable gate switches the amplification means ON for a time just sufficient to amplify the signals; the time the gate switches the amplification means ON corresponding to the elapsed time between the signals; and measuring the duration of the gate.

3. A method for ultrasonic non-destructive testing which comprises: transmitting an initial ultrasonic pulse into a workpiece and receiving corresponding echo pulses from the workpiece; sending the signal in response to the initial pulse and one or more of the echo pulses; controlling the sending of the signal by a variable-width square wave gate; so that the signal will be sent corresponding to a discrete number of pulses; and measuring the duration of the gate.

4. A method for ultrasonic thickness measurement between an entrant surface and a rear surface of a workpiece which comprises:
- transmitting an initial ultrasonic pulse into a workpiece and receiving the corresponding echo pulses from the workpiece;
- amplifying the pulses by an amplification means;
- controlling the ON/OFF condition of the amplification means by adjustment of a time-variable gate; so that the time-variable gate switches the amplification means ON for a time just sufficient to amplify the initial pulse and the first echo pulse; the time the gate switches the amplification means ON corresponding to the elapsed time between the initial pulse and the first corresponding echo pulse.

5. The method of claim 4 further comprising measuring the time the gate switches the amplification means ON.

6. The method of claim 4 wherein the ultrasonic pulse is transmitted by a piezoelectric crystal.

7. The method of claim 4 wherein the time-variable gate is a variblewidth square wave which gates the amplification means ON from an OFF position.

8. The method of claim 7 wherein duration of the square wave can be varied by a potentiometer so that the amplification means is gated ON for only the time necessary to amplify the initial pulse and first echo pulse.

9. The method of claim 4 further comprising counting the number of pulses and sending a signal corresponding to the number of pulses.

10. An apparatus for ultrasonic non-destructive testing which comprises:
- Means for transmitting an initial ultrasonic pulse and receiving corresponding echo pulses; means for sending a signal in response in the initial pulse and one or more echo pulses; a variable-width square wave gate which controls the sending of the signal; so that the signal will be sent corresponding to a discrete number of pulses; and means for measuring the duration of the gate.

11. An apparatus for measuring the time between two or more sequential signals which comprises:
- means for receiving two or more sequential signals;
- means for sending a response signal in response to the received signals;
- a time-variable gate which controls the sending of the response signal; and
- means for measuring the duration of the gate; so that the response signal will be sent corresponding to a discrete number of receive signals and the duration of the gate will correspond to the time between signals.

12. An apparatus for measuring the time between two or more sequential signals which comprises:
- means for receiving two or more sequential signals;
- means for amplifying the signals;
- a time-variable gate which controls the ON/OFF condition of the amplification means; and
- means for measuring the duration of the gate; so that time-variable gate switches the amplification means ON for a time just sufficient to amplify the signals, the time the gate switches the amplification means ON corresponding to the elapsed time between the signals.

13. An apparatus for ultrasonic thickness measurement between an entrant surface and a rear surface of a workpiece which comprises:
- means for transmitting an initial ultrasonic pulse and receiving corresponding echo pulses;
- means for amplifying the pulses; and
- a time-variable gate for controlling the ON/OFF condition of the amplification means;
- so that the time-variable gate switches the amplification means ON for a time just sufficient to amplify the initial pulse and the first echo pulse; the time the gate switches the amplification means ON corresponding to the elapsed time between the initial pulse and the corresponding echo pulse.

14. The apparatus of claim 13 further comprising a means for measuring the time the gate switches the amplification means ON.

15. The apparatus of claim 13 wherein the ultrasonic pulse is transmitted by a piezoelectric crystal.

16. The apparatus of claim 13 wherein the time-variable gate is a variable-width square wave means which gates the amplication means ON from an OFF position.

17. The apparatus of claim 16 wherein duration of the square wave can be varied by a potentiometer so that the amplification means is gated ON for only the time necessary to amplify the initial pulse and first echo pulse.

18. The apparatus of claim 13 further comprising a means for counting the number of pulses and sending a signal corresponding to the number of pulses.

19. An apparatus for ultrasonic thickness measurement comprising: clock pulse generator means for generating a series of timing pulse signals;
- ultrasonic transducer means coupled to the clock pulse generator means and generating ultrasonic pulse signals which are directed into a workpiece, said ultrasonic transducer means generating echo signals representative of ultrasonic signals reflected from the workpiece;
- gate signal generator means coupled to the clock pulse generator means for generating a time-variable gate pulse signal bearing a predetermined relation to each timing pulse signal generated by the clock pulse generator means;
- gated amplifier means coupled to the gate signal generator means and to the ultrasonic transducer means for passing only those signals from the ultrasonic transducer means coinciding in time with each gate pulse signal.

* * * * *